United States Patent

Armentrout et al.

[11] Patent Number: 6,167,113
[45] Date of Patent: Dec. 26, 2000

[54] X-RAY IMAGING SYSTEM FOR DETERMINING AREA DENSITY OF LOW DENSITY SAMPLES

[75] Inventors: Charles J. Armentrout, Ann Arbor; Thomas Basinger, Ypsilanti; James H. Beyer, Ann Arbor; Brian D. Colesa, Chelsea; Paul Olsztyn, Ann Arbor; Karen G. Smith, Brighton; Carl Strandberg, Troy; David Sullivan, Brighton, all of Mich.

[73] Assignee: Pilot Industries, Inc., Dexter, Mich.

[21] Appl. No.: 09/310,278

[22] Filed: May 12, 1999

[51] Int. Cl.[7] .................................................... G01B 15/02
[52] U.S. Cl. .................................. 378/54; 378/51; 378/53
[58] Field of Search .................................. 378/51, 53, 54

[56] References Cited

U.S. PATENT DOCUMENTS

| | | | |
|---|---|---|---|
| 4,150,288 | 4/1979 | Inoue et al. | 378/50 |
| 4,899,298 | 2/1990 | Overhoff | 702/137 |
| 5,381,458 | 1/1995 | Deslattes | 378/207 |
| 5,465,284 | 11/1995 | Karellas | 378/62 |
| 5,491,331 | 2/1996 | Armentrout | 250/214 VT |

*Primary Examiner*—David V. Bruce
*Assistant Examiner*—Allen C Ho
*Attorney, Agent, or Firm*—Gifford, Krass, Groh, Sprinkle, Anderson & Citkowski, P.C.

[57] ABSTRACT

An apparatus and method are disclosed for measuring the area density of a low density material sample. The system includes an x-ray emitter which emits x-rays in the range of 3 kilovolts to 20 kilovolts and the x-rays pass through the sample. An imaging device converts the x-rays which pass through the sample to visible light to produce a visible image corresponding to the sample and in which the visible image has an intensity which varies as a function of the area density across the sample. A camera produces an output signal representative of the intensity of the visible image across the sample while a computer processor processes the signal from the camera after digitization to produce an analysis of the area density of the sample.

17 Claims, 2 Drawing Sheets

X-RAY IMAGING SYSTEM FOR DETERMINING AREA DENSITY OF LOW DENSITY SAMPLES

BACKGROUND OF THE INVENTION

I. Field of the Invention

The present invention relates to a system and method for determining the radiological features of a very low area density sample using an imaging system and a source of low energy x-ray emission. Area density is the amount of sample mass (such as grams) through which the x-ray beam passes, per unit area ($cm^2$) of the beam diameter. Area density is the product of the usual sample volume density ($g/cm^3$) times the path length of sample (cm) along the beam.

II. Description of the Prior Art

There are many previously known x-ray inspection systems for producing images of one sort or another. For example, medical systems using hard or high energy x-rays have long been used to produce images of bones and the like. Such high energy x-rays pass with little attenuation through air and are suitable for imaging very dense and/or very thick objects.

Conversely, soft x-rays, i.e. x-rays having an energy of less than 3 kilovolts, are rarely used in industrial inspection applications. Soft x-rays, however, attenuate rapidly as they pass through air. As such, such industrial applications utilizing soft x-rays must necessarily retain the sample under inspection within a vacuum or non-absorbing atmosphere such as helium in order to prevent excessive attenuation of the soft x-rays.

None of the previously known systems, however, have utilized low energy or border x-rays, i.e. x-rays having an energy level in the range of 3 kilovolts to 15 kilovolts and thus in between soft x-rays and hard x-rays.

SUMMARY OF THE PRESENT INVENTION

The present invention provides both a system and method for x-ray imaging which overcomes all of the above-mentioned disadvantages of the previously known devices.

In brief, the present invention comprises an x-ray source which generates x-rays in the range of 3 kilovolts to 20 kilovolts of energy. Such x-rays fall in the energy range between soft x-rays and hard x-rays. Consequently, these border low energy x-rays are capable of passing a limited distance through air without excessive attenuation and, likewise, can pass through low area density thin objects without excessive attenuation. Higher energy x-rays, while capable of efficiently passing through air, would also pass through very low area density materials without suffering perceptible attenuation. Such unattenuated rays cannot be used for the measurement of sample properties. Such low area density objects have an area density in the range of 0.005 to 1.5 $g/cm^2$.

An imaging device for converting the low energy x-rays to visible light receives the radiation from the x-ray source after passing through the sample. In doing so, the imaging device provides a video image having an intensity across the video image which corresponds to the area density of the corresponding portions of the sample under inspection. For example, an increase in the area density of the sample in one portion of the sample increases the x-ray attenuation and reduces the intensity of the visual image in that area and vice versa. Such a relationship between area density change and intensity variation can be shown to be essentially linear for the samples to be examined by radiation in the low energy range.

In order to process the image produced by the imaging device, a video camera converts the image to an electronic signal that is sent to a computer processor. For example, the camera output signal may be a digital signal or, alternatively, an analog signal which is subsequently converted by conventional means, such as a digitizer, to a digital signal.

The computer processor, under program control, then processes the image from the camera in any desired manner. In one preferred embodiment of the invention, the intensity is calibrated to a standard level by adjusting camera, imager and/or low energy x-ray source to a standard value when a calibration attenuation foil of known thickness and composition is placed in the beam path. Once adjusted to standard brightness, differing samples may be tested at differing times with a given brightness level always indicating the same area density. In this way, the computer processor compares the intensity of the video image with preset ranges of the video intensity. The processor then displays on a color monitor a multi-colored image with different colors representing different ranges of the video intensity of the image sample. Since the intensity of the image correlates directly to the area density of the sample, the displayed image on the color video monitor represents the varying area density of the sample.

Applications of the system and method of the present invention include the inspection of paper, felt, cloth and/or other fiber-structured sheet products which have not been previously inspected by x-rays. The system may also be applied to plastic sheet and composite matrix sheet. The system can, in general, be well applied to any low area density sheet product where consistency in density structure and presence of foreign inclusions, or lack thereof, determine product quality. Likewise, the method and system of the present invention can also be used to inspect thin food products, such as fish patties, to determine if they contain small bones. Likewise, the method and system of the present invention can be used to determine dimensions of injection molded and extruded plastic parts, and to also determine the presence and structures of voids, thickenings and other flaws in the items.

BRIEF DESCRIPTION OF THE DRAWING

A better understanding of the present invention will be had upon reference to the following detailed description when read in conjunction with the accompanying drawing, wherein like reference characters refer to like parts throughout the several views, and in which.

DETAILED DESCRIPTION OF A PREFERRED EMBODIMENT OF THE PRESENT INVENTION

Figure 1:
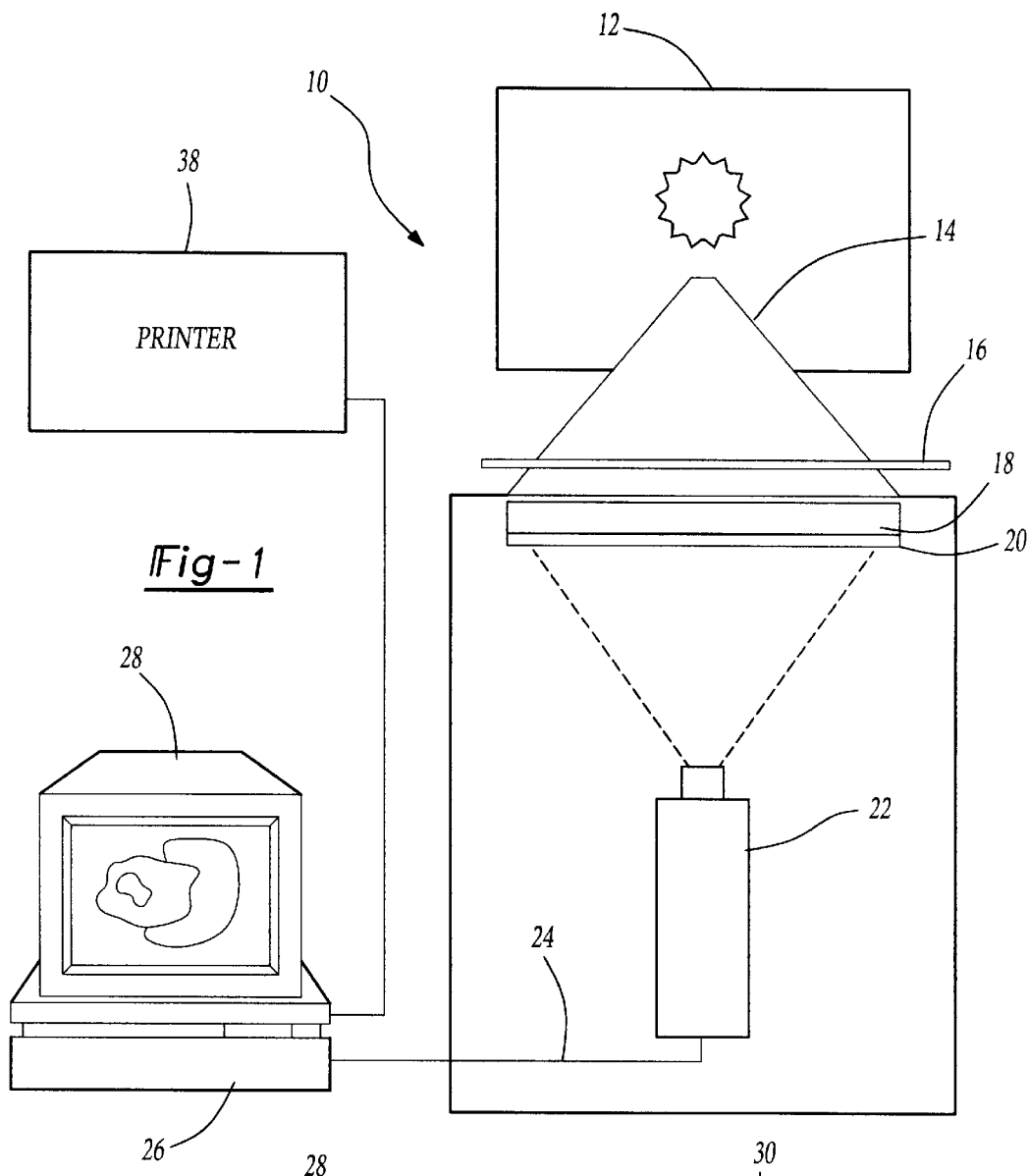
FIG. 1 is a block diagrammatic view illustrating a preferred embodiment of the present invention.

With reference first to FIG. 1, a block diagrammatic view of the x-ray imaging system 10 of the present invention is there shown. The system 10 includes an x-ray source 12 which generates low or border energy x-rays in the range of 3 kilovolts to 20 kilovolts as depicted at 14. As such, the low energy x-rays generated by the source 12 are capable of passing through low area density objects 16, such as paper, having an areal density in the range from below 0.005 g/cm$^2$ to in excess of 1.5 g/cm$^2$. The low energy x-rays 14 are also capable of passing through a short distance of air without excessive attenuation.

Still referring to FIG. 1, an imaging device, such as that shown in U.S. Pat. No. 5,491,331, which issued on Feb. 13, 1996 to Charles Armentrout and entitled "Soft X-Ray Imaging Device" is positioned so that the low energy x-rays 14 passing through the sample 16 impinge upon the imaging device 18 and produce a visual image on the imaging device 18. This visual image will vary in intensity as a function of the area density.

A camera 22 is focused on the optic post 20 of the imaging device 18. The camera 22 generates a signal on its output line 24 representative of the intensity of the image on the optic post 20 of the imaging device 18, and thus of the sample 16. The output signal from the camera 22 is digitized, either internally of the camera or externally by a digitizer such that a pixelized image is produced. For example, assuming that the camera 22 generates a video image that is pixelized into a digital image of 1,000 by 1,000 pixels and each pixel is assigned an intensity or gray level of 0–x, then each of the 1,000,000 pixels in the array has an assigned value of 0–x indicative of and corresponding to the intensity of the image at that pixel where x is function of the resolution of the digitizer. For example, x=255 for an eight bit digitizer, x=1023 for a ten bit digitizer, and so forth.

The output signal on line 24 from the camera 22, after digitization, is coupled as an input signal to a computer processor 26 such as a PC. The digital processor 26 is programmed to compare the intensity of the digitized image to preset intensity ranges stored in the computer processor 26. The computer processor 26 then generates a colorized contour plot indicating the area density rage of the sample 16.

Figure 2:
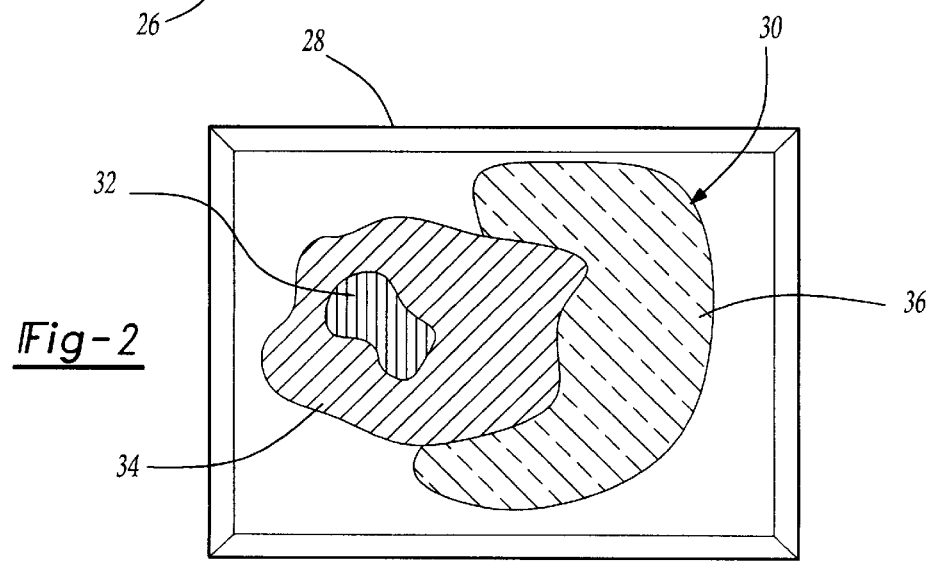
FIG. 2 is a view of an exemplary video display of the present invention.

With reference now to FIG. 2, an exemplary processed video image on the color video monitor 28 is there shown. The video image 30 is an example of a typical implementation of the analysis output of the density contours in the sample 16 from the computer processor 26. The five step intensity contour NN is directly related to the area density contour of the sample 16. The variations are divided into five bands ranging from low intensity (high area density) to high intensity (low density) in the sample image, and colored in the sequence black, blue, green, yellow, and red, respectively. The green band 34 is typically 5% wide and is centered about the overall average density of the sample. The adjacent bands 32 and 36 are the same percent variation, and indicate lighter and heavier area densities. The red band for the lightest density variation extends from the maximum brightest intensity (zero density) to the end of the preceding band. The black band for the minimum intensity (heaviest density) variation extends from zero intensity, maximum thickness to the end of its preceding band.

Alternatively, or optionally, three-dimensional contours can be displayed on the monitor 28. The processor 26 also preferably generates statistical numerical data which is displayed and/or stored and/or printed for the user.

The computer processor 26 optionally generates output signals to a printer 38, preferably a color printer, to record the image 30 in printed form.

Figure 3:
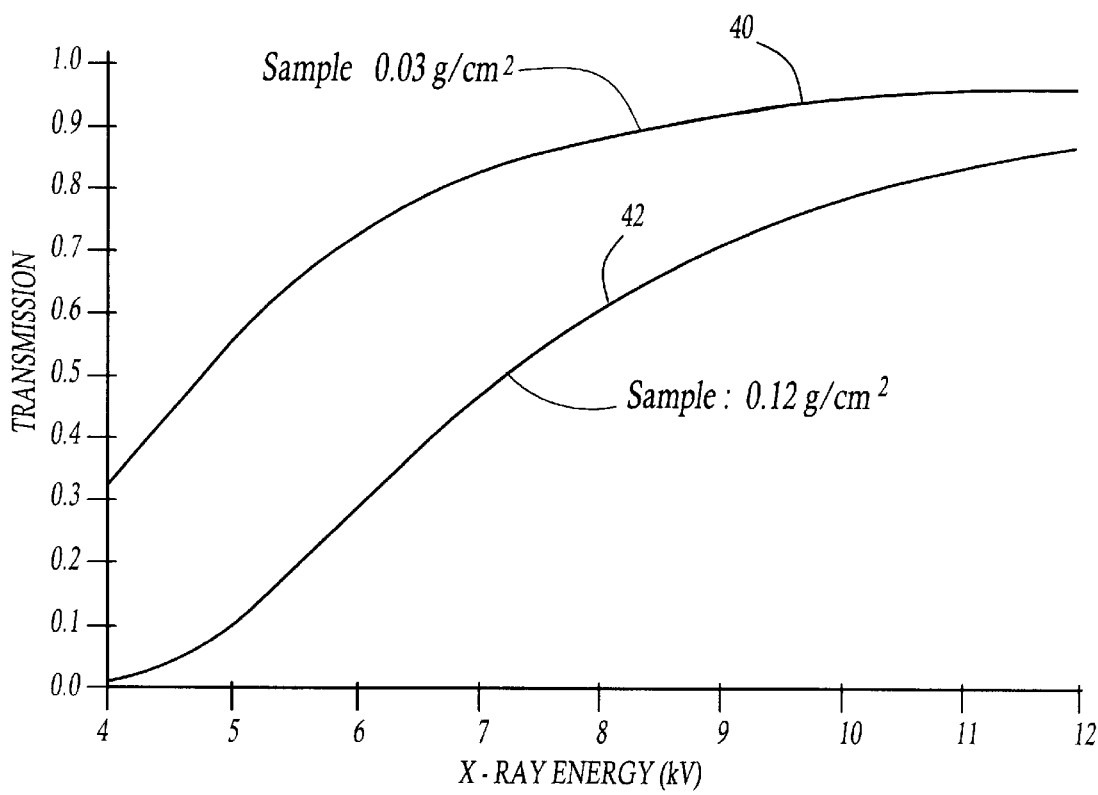
FIG. 3 is a chart illustrating the x-ray transmission through two different samples as a function of the x-ray image.

With reference now to FIG. 3, a graph illustrating the transmission of the low energy x-rays through two samples is there shown as a function of the x-ray energy. A first curve 40 illustrates the transmission as a function of the x-ray energy for a very low areal density sample, i.e. 0.03 g/cm$^2$, while a second curve 42 illustrates the x-ray transmission as a function of x-ray energy for a denser sample, for example 0.12 g/cm$^2$. As can be seen from FIG. 3, the transmission of the low energy x-rays through the sample 16 increases as a function of the x-ray energy and decreases as a function of increased areal density.

In order to optimize the dynamic range of the system 10 for the image acquired by the present invention, FIG. 3 demonstrates that the energy of the x-ray source 12 should be adjusted such that the transmission for the average density of the sample is in the range of 0.4–0.6 (40%–60%) of transmission of the low energy x-rays. In this range, the slope of the graph 40 and 42 is virtually constant so that the intensity of the various pixels of the image produced by the imaging device 18 will vary substantially linearly with the area density of the sample.

Figure 4:
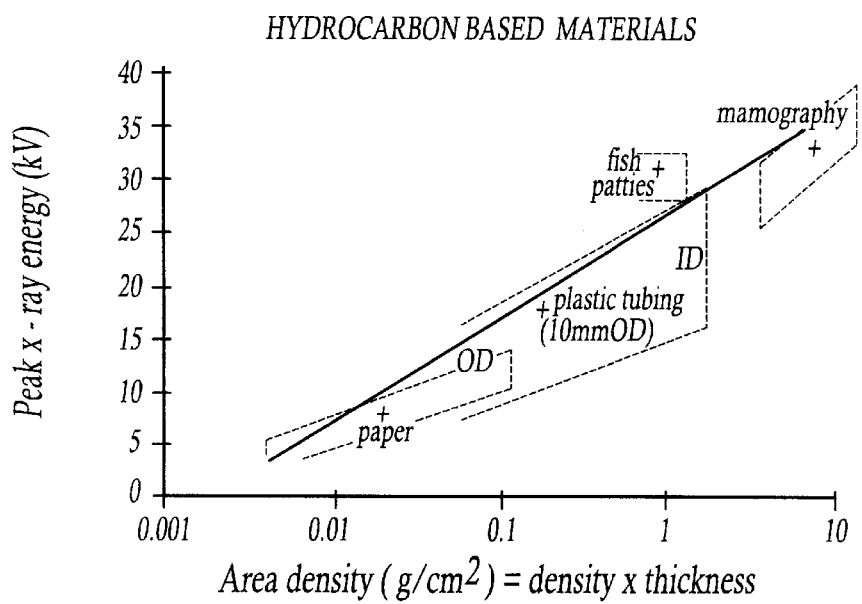
FIG. 4 is a chart illustrating typical set-point or "peak" x-ray source voltage to be used for inspection, as a function of area density for different products.

With reference now to FIG. 4, FIG. 4 is a graph of the x-ray energy versus the area density for various materials.

In the operation of the imaging system of the present invention, it is preferred that the image gain be initially set. In order to accomplish this, an attenuator foil is positioned in the x-ray beam to reduce the intensity of the beam in the same manner that a test sample would attenuate the beam. The attenuator foil is preferably constructed of aluminum or beryllium although other materials can alternatively be used.

Preferably at least two foils are used to set the image gain wherein one foil is thicker than the other foil. With the thinner foil positioned in between the x-ray source and the imaging device and with the energy of the x-ray source set at a low level, for example 8 kev, the intensifier gain is adjusted until the intensity reaches a preset level. At that time, the gain adjustment is noted for subsequent examination of the sample.

The thicker foil is then positioned in between the x-ray source and the intensifier and the energy of the x-ray source is increased to a higher level, for example 15 kev. The intensifier gain is then adjusted to achieve the same intensity as when the lower level was adjusted. The higher energy adjustment is then also noted.

By obtaining a gain adjustment of both low level x-rays as well as high level x-rays, a gain adjustment as a function of the x-ray energy is obtained and this gain adjustment typically is substantially linear. However, for high accuracy systems, three or even more attenuators may be used for the gain adjustment of the system, each attenuator at a different x-ray energy level, and an appropriate curve is fit through the gain determined for each x-ray energy level to account for any nonlinearities.

It is also preferred to find the background image and to correct the image for that background image. The "background" image is the image that is acquired when no sample is in place but when the attenuator foil is present. Each gain setting, furthermore, will have a slightly different background image from the others.

With the attenuator positioned between the x-ray source and the imager, the background image is obtained as an average over many individual frames. This averaging technique will smooth the natural scintillation that arises from an x-ray beam composed of a finite number of photons. The sampled images have been corrected by dividing each sample image pixel by the relative intensity of the same pixel of the background image. By correcting the image for the effect of the background image on a pixel-by-pixel basis, a more accurate final image is obtained by the imaging system.

A primary advantage of the calibration of the imaging system of the present invention utilizing metal foils is that such metal foils do not degrade over time or following bombardment with x-rays. As such, the use of metal attenuator foils enables the overall system of the present invention to be calibrated with respect to preset constants despite aging or degradation of the x-ray source, imaging device or other components of the imaging system. This, in turn, enables high temporal repeatability for the imaging system of the present invention.

The method and system of the present invention has proven to be particularly effective for inspecting very low density objects such as fish products, paper and the like. Furthermore, since the present system utilizes a camera 22, real time processing and inspection of the sample 16 can be achieved.

Having described our invention, many modifications thereto will become apparent to those skilled in the art to which it pertains without deviation from the spirit of the invention as defined by the scope of the appended claims.

We claim:

1. A system for measuring the area density of low density materials sample comprising:

means for generating x-rays having an energy in the range of three kilovolts to twenty kilovolts, said x-rays passing through the sample, means for converting said x-rays to visible light to produce a visible image corresponding to the sample and having an intensity which varies as a function of the area density across the sample, means for producing a digital signal representative of the intensity of the visible image across the sample, means responsive to said digital signal for processing the area density across the sample.

2. The invention as defined in claim 1 wherein said digital signal producing means comprises a camera which generates an analog signal representative of the image, and a digitizer which creates a digitized image of the analog image.

3. The invention as defined in claim 1 wherein said processing means comprises a video monitor and means for displaying said visible image on said video monitor.

4. The invention as defined in claim 1 wherein said processing means further comprises a color video monitor and a computer, said computer programmed to compare said digital signal with predetermined ranges of area density and to generate a video output signal to said monitor having different colors corresponding to different ranges of area density.

5. The invention as defined in claim 1 wherein the sample has a density in the range of less than 0.005 to 1.5 $g/cm^2$.

6. The invention as defined in claim 1 wherein the energy of the x-ray generating means is adjusted to produce a transmission of 40%–60% of the x-rays through the sample.

7. A method for measuring the area density of a low density materials sample comprising the steps of:

generating x-rays having an energy in the range of three kilovolts to twenty kilovolts, passing the x-rays through the sample, converting said x-rays to visible light to produce a visible image corresponding to the sample and having an intensity which varies as a function of the area density across the sample, producing a digital signal representative of the intensity of the visible image across the sample, processing said digital signal to determine the area density across the sample.

8. The invention as defined in claim 7 wherein said processing step further comprises the step of displaying said visible image on said video monitor.

9. The invention as defined in claim 7 wherein said processing step further comprises the steps of comparing said digital signal with predetermined ranges of area density and generating a color video output signal to a color video monitor, said color video output signal having different colors corresponding to different ranges of area density.

10. The invention as defined in claim 7 wherein the sample has a density in the range of less than 0.005 to 1.5 $g/cm^2$.

11. The invention as defined in claim 7 and comprising the step of adjusting the energy of the x-ray generating means to produce transmission of 40%–60% of the x-rays through the sample.

12. The invention as defined in claim 7 wherein said processing step further comprises the steps of comparing said digital signal with predetermined ranges of area density and generating a video output signal to a video monitor representative of a three-dimensional contour, corresponding to different ranges of area density.

13. The invention as defined in claim 7 wherein said processing step further comprises the step of generating statistical numerical data corresponding to said digital signal.

14. A method for calibrating a soft x-ray imaging system of the type having an x-ray source and an imaging device comprising the steps of:

placing a first foil between said source and said imaging device, adjusting the source to a first predetermined power level, determining the imager gain to achieve a preset image intensity, placing a second foil between said source and said imaging device, adjusting the source to a second predetermined power level, said second predetermined power level being different than said first predetermined power level, and determining the imager gain to achieve said preset image intensity, whereby a graph of imager gain versus power level is obtained.

15. The method as defined in claim 14 wherein one of said foils is made of aluminum.

16. The method as defined in claim 14 wherein one of said foils is made of beryllium.

17. The method as defined in claim 14 and further comprising the steps of:

measuring the background image, and adjusting the image intensity on a pixel-by-pixel basis as a function of the background image on a pixel-by-pixel image.

* * * * *